United States Patent
Tsuda et al.

(10) Patent No.: US 6,779,396 B2
(45) Date of Patent: Aug. 24, 2004

(54) METHOD FOR MEASURING FLOW WITHIN AN OPEN TUBE

(75) Inventors: Takao Tsuda, 3102, Kaguyama 2-chome, Nisshin-shi, Aichi (JP); Motonori Munesue, 178-11, Kitashinmachi 6-chome, Matsubara-shi, Osaka (JP)

(73) Assignees: Takao Tsuda, Aichi (JP); Chemco Scientific Co. Ltd., Osaka (JP); Motonori Munesue, Osaka (JP)

( * ) Notice: Subject to any disclaimer, the term of this patent is extended or adjusted under 35 U.S.C. 154(b) by 0 days.

(21) Appl. No.: 10/119,131

(22) Filed: Apr. 8, 2002

(65) Prior Publication Data

US 2003/0188575 A1 Oct. 9, 2003

(51) Int. Cl.[7] .................................................. G01F 1/68
(52) U.S. Cl. ................................................ 73/204.27
(58) Field of Search ........................ 73/204.27, 204.26, 73/204.23, 204.19, 204.25, 204.15

(56) References Cited

U.S. PATENT DOCUMENTS

| | | | | |
|---|---|---|---|---|
| 4,217,910 A | * | 8/1980 | Khalil | ........................ 600/483 |
| 5,260,665 A | * | 11/1993 | Goldberg et al. | ........... 324/636 |
| 5,936,156 A | * | 8/1999 | Roberts et al. | .......... 73/204.19 |
| 6,085,588 A | * | 7/2000 | Khadkikar et al. | ...... 73/204.27 |
| 6,234,016 B1 | * | 5/2001 | Bonne et al. | ............ 73/204.26 |
| 6,318,171 B1 | * | 11/2001 | Suzuki | ................... 73/204.27 |
| 6,354,150 B1 | * | 3/2002 | Rudent et al. | ............. 73/202.5 |
| 6,386,050 B1 | * | 5/2002 | Yin et al. | ................ 73/861.95 |

* cited by examiner

Primary Examiner—Edward Lefkowitz
Assistant Examiner—Jewel V. Thompson
(74) Attorney, Agent, or Firm—Akin Gump Strauss Hauer & Feld LLP (57) ABSTRACT

A change in physical properties of a fluid within an open tube which is caused by heating an arbitrary portion in the open tube by heating means is detected by using a detector disposed with a predetermined spacing from the arbitrary portion, thereby measuring the flow in the open tube. The present invention provides a method for measuring flow within an open tube, in which a mechanical error and contamination of a passage do not occur, as a method for measuring flow within an open tube having a very small diameter provided for the separation analysis field and chemosynthesis field.

40 Claims, 8 Drawing Sheets

METHOD FOR MEASURING FLOW WITHIN AN OPEN TUBE

BACKGROUND OF THE INVENTION AND DESCRIPTION OF RELATED ART

The present invention relates to flow measuring method suitable for measurement of flow within an open tube having a very small diameter, which may be provided for a separation analysis field such as liquid chromatography and electrochromatography, a chemosynthesis field, and the like.

Conventionally, the flow within an open tube having a very small diameter is measured by methods such as: a first method of calculating volume of a discharge portion of a pumping device; a second method of attaching a fan to a passage and calculating the flow from the revolution of the fan; a third method of inserting two filaments, heating one of them, and calculating the flow from speed of conduction of heat to the other filament; and a fourth method of intermittently passing a substance different from a fluid, such as bubbles, into a passage and converting pass time into flow by using an optical sensor.

However, in the conventional methods of measuring flow within an open tube, the first and second methods have a problem such that a mechanical error may occur in a measurement value. The third method has a problem that the filaments are worn out and cut. The fourth method has problems such that, since a foreign matter is inserted into a passage, it is difficult to insert the foreign matter and that the passage is contaminated due to the insertion of the foreign matter. Consequently, any of the methods is not suitable for the separation analysis field, chemosynthesis field, and the like.

An object of the present invention is therefore to provide a method for measuring flow within an open tube, in which a mechanical error and contamination of a passage do not occur, as a method for measuring flow within an open tube having a very small diameter provided for the separation analysis field and chemosynthesis field.

SUMMARY OF THE INVENTION

To achieve the above-mentioned object, according to a method for measuring flow within an open tube of the present invention, a change in physical properties of a fluid within an open tube which is caused by heating an arbitrary portion in the open tube by heating means is detected by using a detector disposed with a predetermined spacing from the heating portion, thereby measuring the flow in the open tube.

Further, according to a method for measuring flow within an open tube of the present invention, a change in physical properties of a fluid within an open tube which is caused by heating an arbitrary portion in the open tube by heating means is detected by using a detector disposed with a predetermined spacing from the heating portion, thereby measuring the flow within the tube and, further, the flow is computing-processed by a computer system to thereby obtain a flow signal.

According to a method for measuring flow within an open tube of the present invention, a time difference between time at which heating is started by the heating means and time at which a signal is detected by the detector is measured.

The heating means used for the measuring method of the present invention may be current-passing heating means or light-condensing heating means. The heating by the heating means may be performed by a gradient voltage.

The open tube used for the measuring method of the present invention may be a capillary column for use in capillary electrophoresis, capillary liquid chromatography, and the like, a pre-column or a post column for use in gas chromatography, liquid chromatography, and the like, a catheter or a tube connected to a catheter for use in a system for automatically supplying chemical to an animal or a human being, a micropipet or a tube connected to a micropipet for use in study of life science, and the like.

A change in physical properties of the fluid within the tube in the measuring method of the present invention may be a change in temperature or occurrence of bubbles.

Further, a detector for use in the measuring method of the present invention may be constructed by a combination of an infrared LED and a photodiode.

The above and other objects and effects of the present invention will become apparent in the following description with reference to the accompanying drawings.

DETAILED DESCRIPTION OF THE INVENTION

Figure 1:
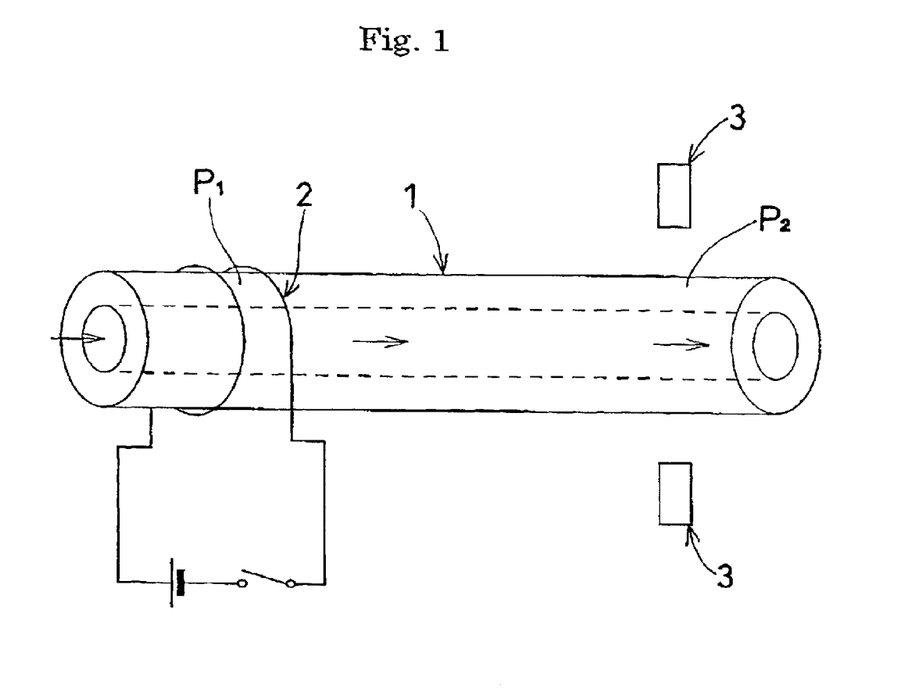
FIG. 1 is a schematic diagram showing an example of an apparatus for carrying out a method for measuring flow within an open tube of the present invention.

FIG. 1 is a schematic diagram of an example of an apparatus for carrying out a method for measuring flow within an open tube of the present invention. By heating means 2 for passing a current to a nichrome wire wound around an arbitrary portion P1 in the upstream part of an open tube 1 taking the form of a capillary column, the portion P1 in the open tube 1 may be heated. A detector 3 is disposed in an arbitrary portion P2 in the downstream part of the open tube 1 with a predetermined spacing from the portion P1 in the upstream part so that a change in physical properties of a fluid within the tube due to the heating may be detected by the detector 3.

Figure 2:
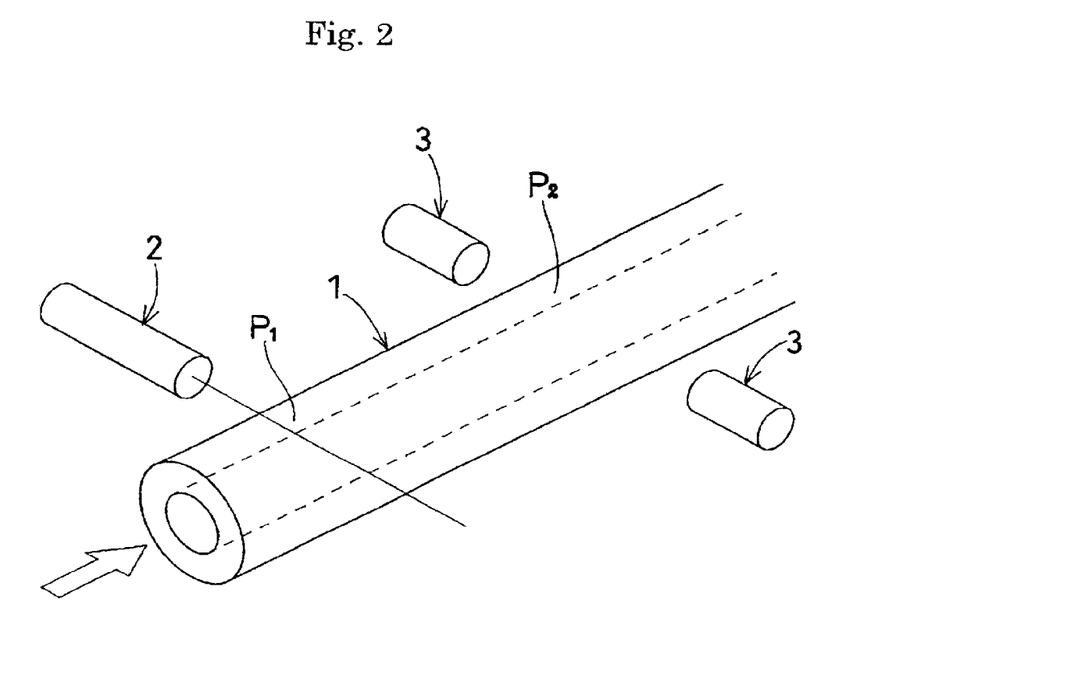
FIG. 2 is a schematic diagram showing another example of an apparatus for carrying out a method for measuring flow within an open tube of the present invention.

FIG. 2 shows another example of an apparatus for carrying out the method for measuring flow within an open tube of the present invention. By the heating means 2 for irradiating an arbitrary portion P1 in the upstream part of the open tube 1 taking the form of a pre-column with a laser beam, the portion P1 in the open tube 1 may be heated. A detector 3 is disposed in an arbitrary portion P2 in the downstream part of the open tube 1 with a predetermined spacing from the portion P1 in the upstream part so that a change in physical properties of a fluid within the tube due to the heating may be detected by the detector 3.

Figure 3:
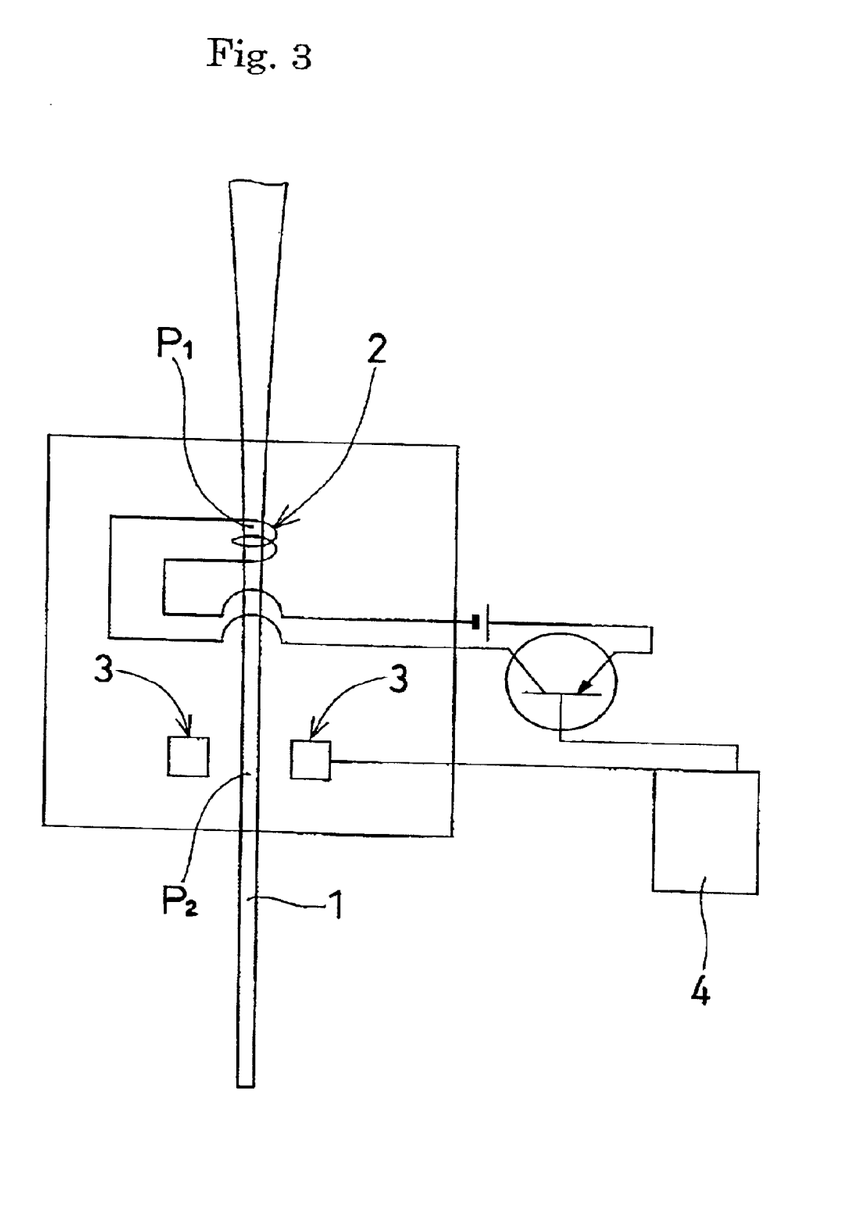
FIG. 3 is a schematic diagram showing further another example of an apparatus for carrying out a method for measuring flow within an open tube of the present invention.

FIG. 3 shows further another example of an apparatus for carrying out the method for measuring flow within an open tube of the present invention. By the heating means 2 for passing a current to a nichrome wire wound around an arbitrary portion P1 in the upstream part of the open tube 1 taking the form of a micropipet, the portion P1 in the open tube 1 may be heated. A detector 3 is disposed in an arbitrary portion P2 in the downstream part of the open tube 1 with a predetermined spacing from the portion P1 in the upstream part so that a change in physical properties of a fluid within the tube due to the heating may be detected by the detector 3. Further, a computer system 4 is assembled between the heating means 2 and the detector 3. By the computer system 4, a computing process is performed so that a flow signal may be obtained.

In any of the apparatuses shown in FIGS. 1 to 3, the arbitrary portion P2 in the downstream part of the open tube 1 may be an outlet of the open tube 1.

The material, length, and inside diameter of the open tube 1 may be arbitrarily selected so as to be adapted to any fluid. For example, the open tube 1 may take the form of a capillary column for use in capillary electrophoresis, capillary liquid chromatography, and the like, a pre-column or a post column for use in gas chromatography, liquid chromatography, and the like, a catheter for use in a system for automatically supplying chemical to an animal or a human being, a micropipet for use in study of life science, and the like.

The heating means 2 may take any form as long as it may heat a fluid within a tube from the outside of the open tube 1 and may be realized by, for example, current-passing heating means or light-condensing heating means. The current-passing heating means may pass current to a heating element such as a nichrome wire. The light-condensing heating means may condense a laser beam, white light, infrared light, or the like. When the heating means 2 is realized by the current-passing heating means or light-condensing heating means, the heating means 2 may easily heat an arbitrary portion of the open tube from the outside, and no contamination occurs in a passage.

Further, the heating means 2 may heat not by supplying current at a constant voltage but by supplying current at a gradient voltage.

As the detector 3, for example, a combination of an infrared LED and a photodiode may be used. The detector 3 is not limited to an optical detector but may be an electric detector or other proper means. When the detector 3 is constructed by a combination of an infrared LED and a photodiode, the size of the detector 3 may be reduced and it becomes easier to dispose the detector 3 to the open tube 1.

Examples of the fluid within the tube are various developing agents, reaction reagents, remedy chemicals, and inspection chemicals. However, the fluid is not limited to those examples but any fluid may be used. A change in physical properties of a fluid within a tube may be a change in temperature or occurrence of bubbles. Alternatively, the change may be a change in electric resistance or the like which cannot be detected by an optical detector.

In the apparatus constructed as described above, while passing the fluid into the open tube 1, the absorbance of the fluid is successively measured by the detector 3 at the position P2 in the downstream part of the open tube 1. In the apparatuses shown in FIGS. 1 and 3, a current is supplied to the nichrome wire wound around the open tube 1 for a unit time. In the apparatus shown in FIG. 2, the open tube 1 is irradiated with a laser beam for a unit time. Consequently, the portion P1 in the upstream portion of the open tube 1 is locally heated. In association with the local heating, the fluid passing through the open tube 1 is heated, and the refractive index of the liquid changes as the heating develops.

When the liquid with the changed refractive index passes through the portion P2, the change in absorbance is detected by the detector 3. By the difference between the time of detection by the detector 3 and the time at which the heating is started by the heating means 2, the flow within the tube of the liquid may be calculated.

In the case of supplying a current to the nichrome wire wound around the open tube 1 for a unit time, a current is supplied at, not a constant voltage but, a gradient voltage, so that the absolute flow may be calculated from a detection pattern of the detection signal by the gradient voltage.

Examples of the method for measuring flow within an open tube of the present invention will now be described.

EXAMPLE 1

Figure 4:
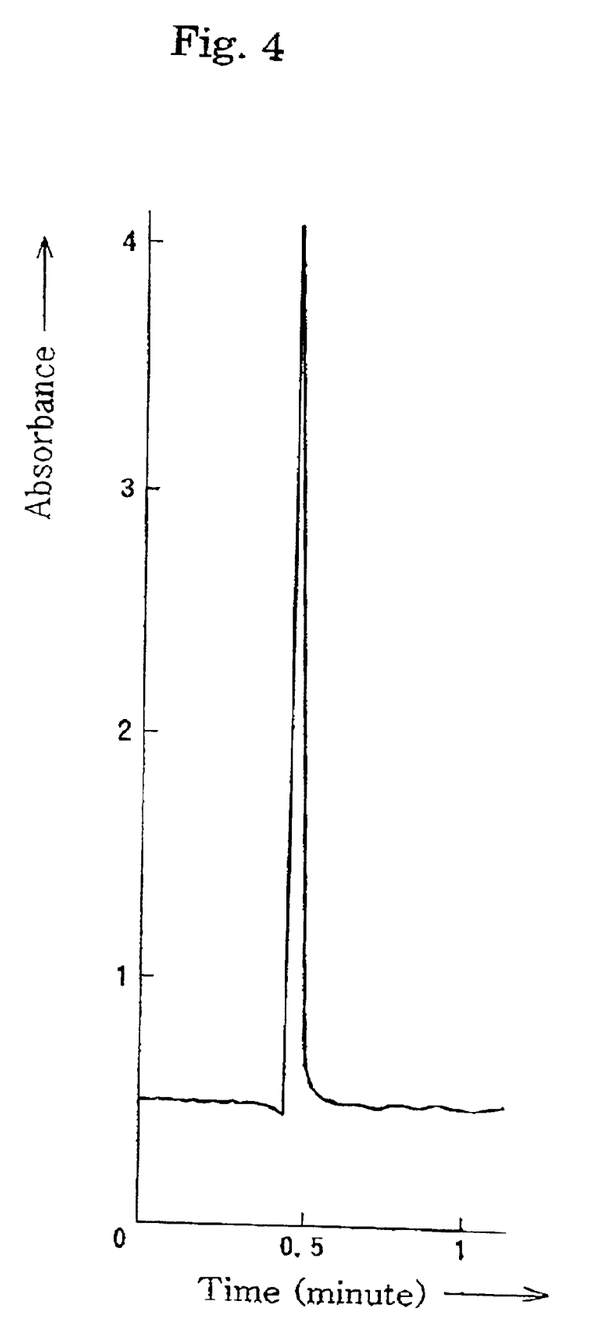
FIG. 4 is a diagram showing a measurement result of absorbance in a first example of the method for measuring flow within an open tube of the present invention.

FIG. 4 shows the result of successively measuring absorbance when, in the apparatus shown in FIG. 1, the inside diameter of the open tube 1 was set to 100 $\mu$m, the spacing between the portion P1 in the upstream part of the open tube 1 and the portion P2 in the downstream part of the open tube 1 was set to 30 mm, and a direct current of 0.41 A was supplied to a nichrome wire wound around the open tube 1 at a voltage of 1.2V for three seconds. It is understood from FIG. 4 that the change in absorbance due to bubbles generated from the fluid was detected in 0.5 minute. As a result, the flow of the liquid passing through the open tube 1 could be calculated as 470 nl/min.

EXAMPLE 2

Figure 5:
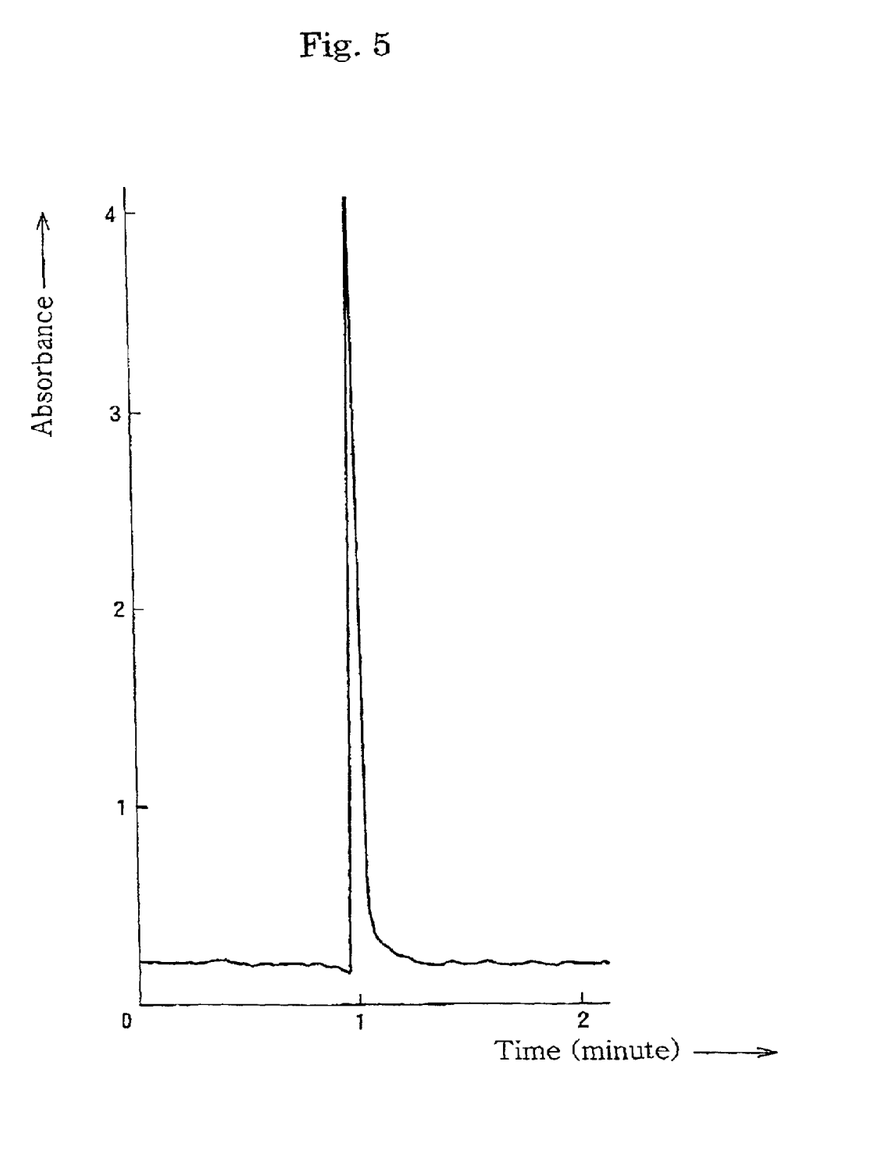
FIG. 5 is a diagram showing a measurement result of absorbance in a second example of the method for measuring flow within an open tube of the present invention.

FIG. 5 shows the result of successively measuring absorbance when, in the apparatus shown in FIG. 1, the inside diameter of the open tube 1 was set to 100 $\mu$m, the spacing between the portion P1 in the upstream part of the open tube 1 and the portion P2 in the downstream part of the open tube 1 was set to 30 mm, and a direct current of 0.41 A was supplied to a nichrome wire wound around the open tube 1 at a voltage of 1.2V for eight seconds. It is understood from FIG. 5 that the change in absorbance caused by bubbles generated from the fluid was detected in one minute. As a result, the flow of the liquid passing through the open tube 1 could be calculated as 235 nl/min.

EXAMPLE 3

Figure 6:
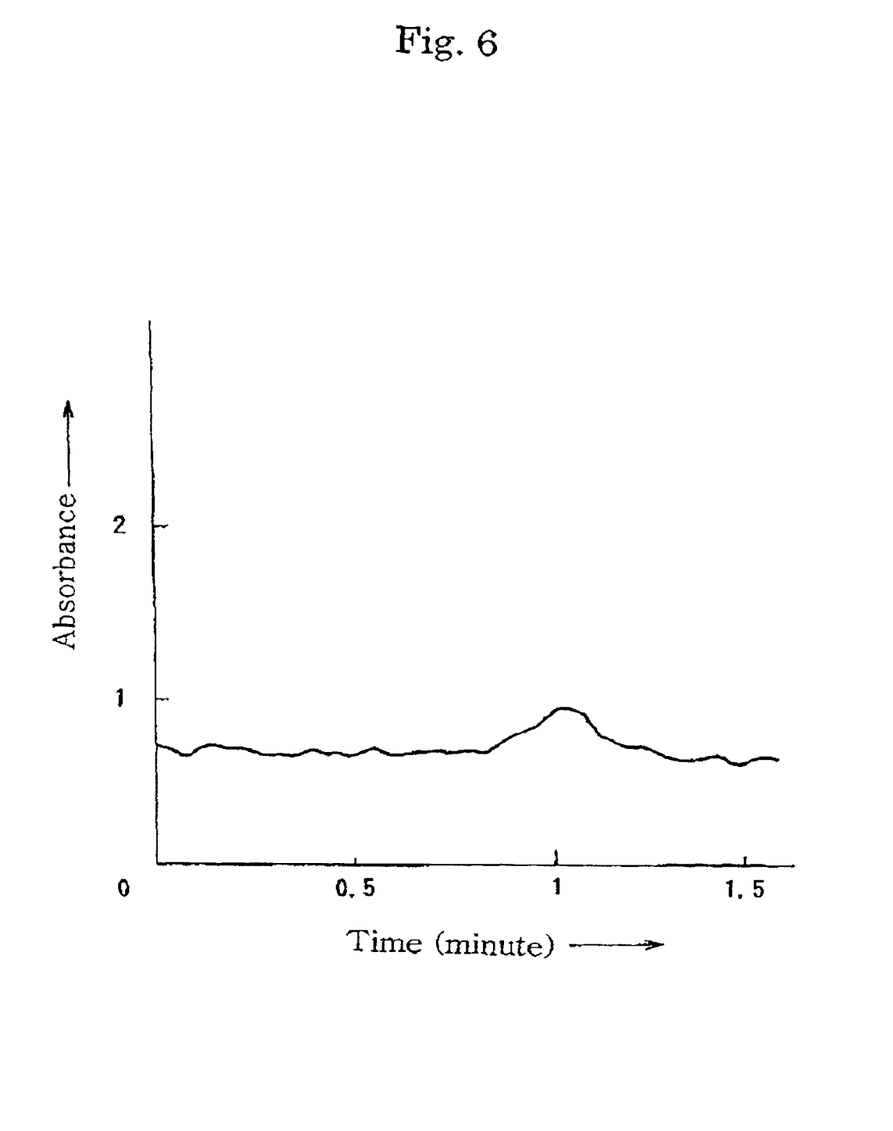
FIG. 6 is a diagram showing a measurement result of absorbance in a third example of the method for measuring flow within an open tube of the present invention.

FIG. 6 shows the result of measuring absorbance when, in the apparatus shown in FIG. 1, the inside diameter of the open tube 1 was set to 100 $\mu$m, the spacing between the portion P1 in the upstream part of the open tube 1 and the portion P2 in the downstream part of the open tube 1 was set to 30 mm, and a direct current of 0.31 A was supplied to a nichrome wire wound around the open tube 1 at a voltage of 1.0V for 15 seconds. It is understood from FIG. 6 that the change in absorbance due to increase in temperature of the fluid was detected in one minute. As a result, the flow of the liquid passing through the open tube 1 could be calculated as 235 nl/min.

EXAMPLE 4

Figure 7:
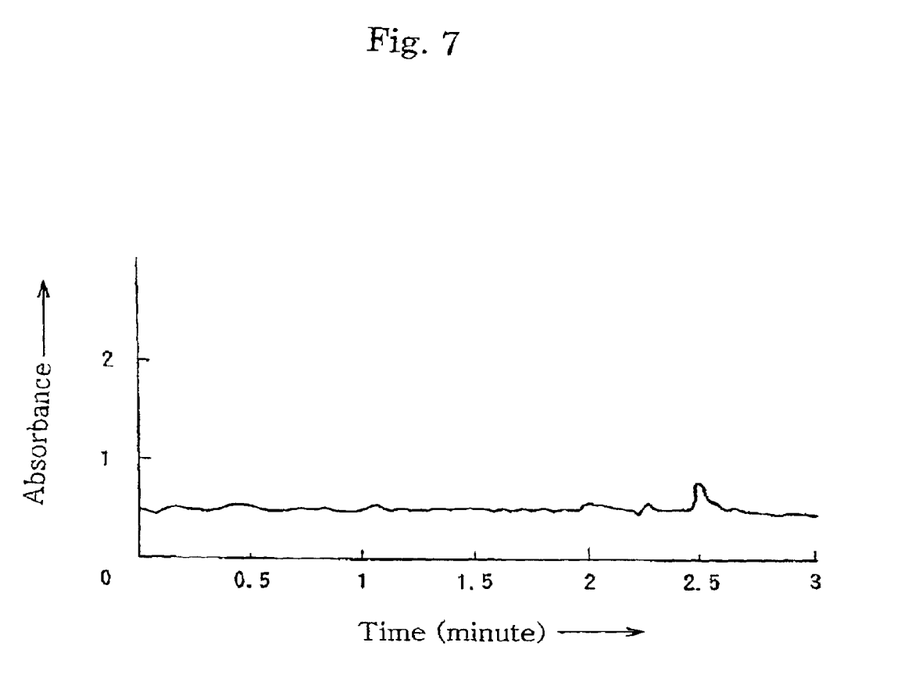
FIG. 7 is a diagram showing a measurement result of absorbance in a fourth example of the method for measuring flow within an open tube of the present invention.

FIG. 7 shows the result of measuring absorbance when, in the apparatus shown in FIG. 1, the inside diameter of the open tube 1 was set to 100 μm, the spacing between the portion P1 in the upstream part of the open tube 1 and the portion P2 in the downstream part of the open tube 1 was set to 30 mm, and a direct current of 0.36 A was supplied to a nichrome wire wound around the open tube 1 at a voltage of 1.1V for 20 seconds. It is understood from FIG. 7 that the change in absorbance due to the increase in temperature of the fluid was detected in 2.5 minutes. As a result, the flow of the liquid passing through the open tube 1 could be calculated as 94 nl/min.

EXAMPLE 5

Figure 8:
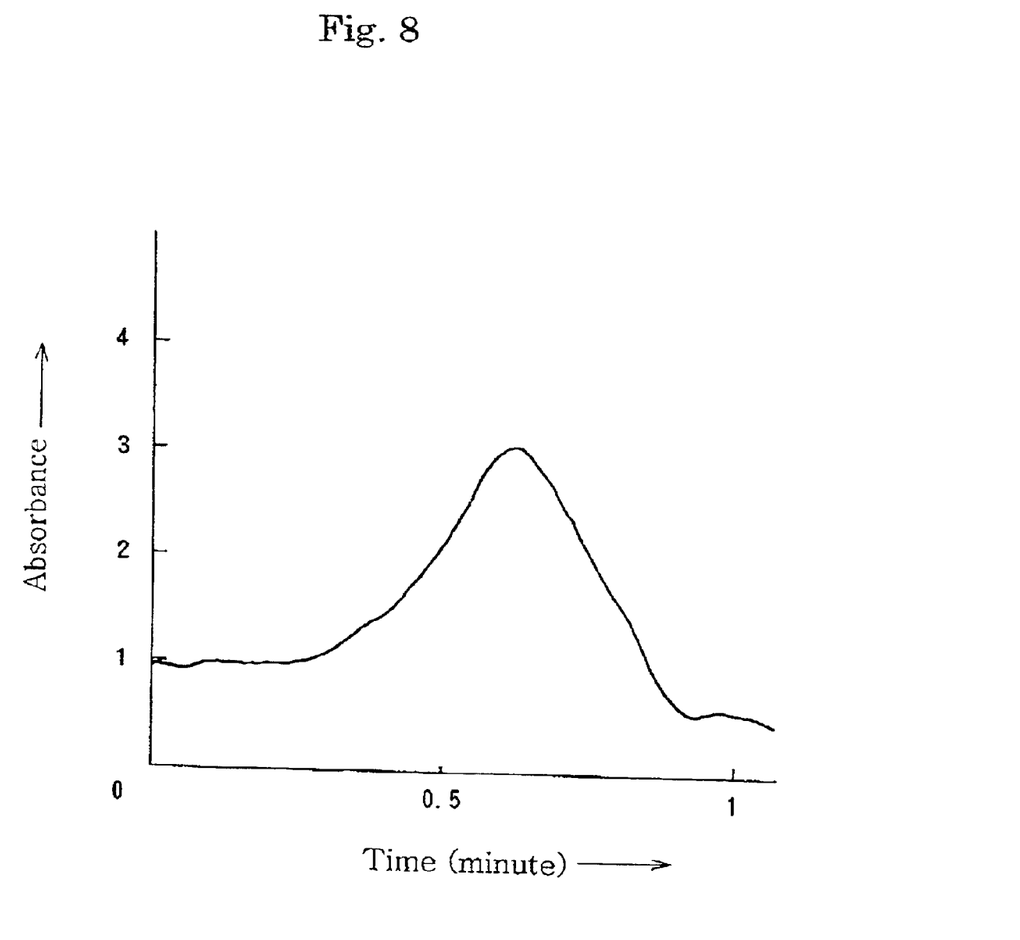
FIG. 8 is a diagram showing a measurement result of absorbance in a fifth example of the method for measuring flow within an open tube of the present invention.

FIG. 8 shows the result of measuring absorbance when, in the apparatus shown in FIG. 3, the inside diameter of the open tube 1 was set to 100 μm, the spacing between the portion P1 in the upstream part of the open tube 1 and the portion P2 in the downstream part of the open tube 1 was set to 30 mm, the voltage was supplied to a nichrome wire wound around the open tube 1 while increasing the voltage from 0V to 0.5V in 20 seconds and decreasing the voltage from 0.5V to 0V in 20 seconds. From FIG. 8, by using a detection pattern of the change in absorbance due to increase in temperature of the fluid, an accurate heating time point may be recognized and the flow may be calculated. Further, the detection pattern is computing-processed by the computer system 4, thereby obtaining a flow signal. The flow may be thereby controlled.

Since the present invention is constructed as described above, the method for measuring flow within an open tube without a mechanical error and occurrence of contamination in a passage may be provided.

Therefore, variations in analysis precision due to fluctuations in the flow in the separation analysis field may be solved, information of the flow may be obtained on-time for an analysis method of capillary electrophoresis or the like, so that the reliability of a small amount chromatography is improved. Precise flow measurement and a flow control of a pre-column reaction and a post-column reaction in the separation analysis field may be performed. Further, in the chemosynthesis field, management of the action of a chemical automatic supply system and the like may be performed, and supply or the like of a reagent may be finely controlled.

What is claimed is:

1. A method for measuring flow within an open tube having no insulating layer comprising:
    heating an arbitrary portion in the open rube by heating means to make a change in physical properties of a fluid within the open tube;
    providing an optical detector disposed with a predetermined spacing from the arbitrary portion; and
    detecting the change by using the optical detector to measure the flow within the open tube.

2. The method according to claim 1, wherein a time difference between a time at which heating is started by the heating means and a time at which a signal is detected by the optical detector is measured.

3. The method according to claim 1, wherein the heating means is current-passing heating means or light-collecting heating means.

4. The method according to claim 1, wherein the heating by the heating means is performed by a gradient voltage.

5. The method according to claim 1, wherein the open tube is a capillary column for use in capillary electrophoresis, capillary liquid chromatography, and the like.

6. The method according to claim 1, wherein the open tube is a pre-column or a post column for use in gas chromatography, liquid chromatography, and the like.

7. The method according to claim 1, wherein the open tube is a catheter or a tube connected to a catheter for use in a system for automatically supplying chemical to an animal or a human being.

8. The method according to claim 1, wherein the open tube is a micropipet or a tube connected to a micropipet for use in study of life science and the like.

9. The method according to claim 1, wherein the change in physical properties of the fluid within the tube is a change in temperature or occurrence of bubbles.

10. The method according to claim 1, wherein the optical detector is constructed by a combination of an infrared LED and a photodiode.

11. A method for measuring flow within an open tube having no insulating layer comprising:
    heating an arbitrary portion in the open tube by heating means to make a change in physical properties of a fluid within the open tube;
    providing an optical detector disposed with a predetermined spacing from the arbitrary portion;
    detecting the change by using the optical detector to measure the flow within the open tube; and
    performing a computing process of the flow by a computer system to obtain a flow signal.

12. The method according to claim 11, wherein a time difference between a time at which heating is started by the heating means and a time at which a signal is detected by the optical detector is measured.

13. The method according to claim 11, wherein the heating means is current-passing heating means or light-collecting heating means.

14. The method according to claim 11, wherein the heating by the heating means is performed by a gradient voltage.

15. The method according to claim 11, wherein the open tube is a capillary column for use in capillary electrophoresis, capillary liquid chromatography, and the like.

16. The method according to claim 11, wherein the open tube is a pre-column or a post column for use in gas chromatography, liquid chromatography, and the like.

17. The method according to claim 11, wherein the open tube is a catheter or a tube connected to a catheter for use in a system for automatically supplying chemical to an animal or a human being.

18. The method according to claim 11, wherein the open tube is a micropipet or a tube connected to a micropipet for use in study of life science and the like.

19. The method according to claim 11, wherein the change in physical properties of the fluid within the tube is a change in temperature or occurrence of bubbles.

20. The method according to claim 11, wherein the optical detector is constructed by a combination of an infrared LED and a photodiode.

21. The method according to claim 1, wherein the heating means is local heating performed by a current passing means comprising a single-wound coil.

22. The method according to claim 11, wherein the heating means is local heating performed by a current passing means comprising a single-wound coil.

23. A method for measuring flow within an open tube comprising:
    heating an arbitrary portion in the open tube by heating means to make a change in occurrence of bubbles of a fluid within the open tube;

providing a detector disposed with a predetermined spacing from the arbitrary portion; and detecting the change by using the detector to measure the flow within the open tube.

24. The method according to claim 23, wherein a time difference between a time at which heating is started by the heating means and a time at which a signal is detected by the detector is measured.

25. The method according to claim 23, wherein the heating means is current-passing heating means or light-collecting heating means.

26. The method according to claim 23, wherein the heating by the heating means is performed by a gradient voltage.

27. The method according to claim 23, wherein the open tube is a capillary column for use in capillary electrophoresis, capillary liquid chromatography, and the like.

28. The method according to claim 23, wherein the open tube is a pre-column or a post column for use in gas chromatography, liquid chromatography, and the like.

29. The method according to claim 23, wherein the open tube is a catheter or a tube connected to a catheter for use in a system for automatically supplying chemical to an animal or a human being.

30. The method according to claim 23, wherein the open tube is a micropipet or a tube connected to a micropipet for use in study of life science and the like.

31. The method according to claim 23, wherein the detector is constructed by a combination of an infrared LED and a photodiode.

32. A method for measuring flow within an open tube comprising:

heating an arbitrary portion in the open tube by heating means to make a change in occurrence of bubbles of a fluid within the open tube;

providing a detector disposed with a predetermined spacing from the arbitrary portion; and detecting the change by using the detector to measure the flow within the open tube; and performing a computing process of the flow by a computer system to obtain a flow signal.

33. The method according to claim 32, wherein a time difference between a time at which heating is started by the heating means and a time at which a signal is detected by the detector is measured.

34. The method according to claim 32, wherein the heating means is current-passing heating means or light-collecting heating means.

35. The method according to claim 32, wherein the heating by the heating means is performed by a gradient voltage.

36. The method according to claim 32, wherein the open tube is a capillary column for use in capillary electrophoresis, capillary liquid chromatography, and the like.

37. The method according to claim 32, wherein the open tube is a pre-column or a post column for use in gas chromatography, liquid chromatography, and the like.

38. The method according to claim 32, wherein the open tube is a catheter or a tube connected to a catheter for use in a system for automatically supplying chemical to an animal or a human being.

39. The method according to claim 32, wherein the open tube is a micropipet or a tube connected to a micropipet for use in study of life science and the like.

40. The method according to claim 32, wherein the detector is constructed by a combination of an infrared LED and a photodiode.

\* \* \* \* \*